United States Patent
Kim et al.

(10) Patent No.: US 10,059,926 B2
(45) Date of Patent: Aug. 28, 2018

(54) MUTANT LACTATE DEHYDROGENASE

(71) Applicant: Samsung Electronics Co., Ltd., Suwon-si, Gyeonggi-do (KR)

(72) Inventors: Jinha Kim, Namyangju-si (KR);
Kwangmyung Cho, Seongnam-si (KR);
Soonchun Chung, Seoul (KR);
Yukyung Jung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/167,889

(22) Filed: May 27, 2016

(65) Prior Publication Data
US 2016/0348079 A1 Dec. 1, 2016

(30) Foreign Application Priority Data

May 28, 2015 (KR) .................. 10-2015-0075373

(51) Int. Cl.
*C12N 9/04* (2006.01)
*C12Q 1/32* (2006.01)
*C12P 7/56* (2006.01)

(52) U.S. Cl.
CPC .............. *C12N 9/0006* (2013.01); *C12P 7/56* (2013.01); *C12Q 1/32* (2013.01); *C12Y 101/01028* (2013.01); *G01N 2333/904* (2013.01)

(58) Field of Classification Search
None
See application file for complete search history.

(56) References Cited

U.S. PATENT DOCUMENTS

| | | | |
|---|---|---|---|
| 7,964,382 B2 | 6/2011 | Ishida et al. | |
| 8,343,764 B2 * | 1/2013 | Abad | C07K 14/415 435/419 |
| 8,426,191 B2 | 4/2013 | Zhou et al. | |
| 8,822,195 B2 | 9/2014 | Sawai et al. | |
| 2009/0275095 A1 | 11/2009 | Ishida et al. | |
| 2009/0305369 A1 | 12/2009 | Donaldson et al. | |
| 2010/0203602 A1 | 8/2010 | Zhou et al. | |
| 2010/0209986 A1 | 8/2010 | Liao et al. | |
| 2012/0070871 A1 | 3/2012 | Sawai et al. | |

FOREIGN PATENT DOCUMENTS

JP  2011-522541 A  8/2011

OTHER PUBLICATIONS

Nielsen et al., Engineering alternative butanol production platforms in heterologous bacteria, *Metabolic Engineering* 11: 262-273 (2009).
Shen et al., Driving Forces Enable High-Titer Anaerobic 1-Butanol Synthesis in *Escherichia coli*, *Applied and Environmental Microbiology*, 77(9) 2905-2915 (2011).
Zhou et al., Production of Optically Pure D-Lactic Acid in Mineral Salts Medium by Metabolically Engineered *Escherichia coli*, *Applied and Environmental Microbiology*, 69(1): 399-407 (2003).
Zhou et al., Fermentation of 12% (w/v) glucose to 1.2 M lactate by *Escherichia coli* strain SZ194 using mineral salts medium, *Biotechnology Letters*, 28: 663-670 (2006).

* cited by examiner

*Primary Examiner* — Hope Robinson
(74) *Attorney, Agent, or Firm* — Leydig, Voit & Mayer, Ltd.

(57) ABSTRACT

A method of screening a microorganism having a mutant lactate dehydrogenase with increased activity, a mutant lactate dehydrogenase polypeptide, a polynucleotide and vector encoding same, and a microorganism that expresses the lactate dehydrogenase mutant, and a method of producing lactate using the microorganism.

3 Claims, 1 Drawing Sheet

Specification includes a Sequence Listing.

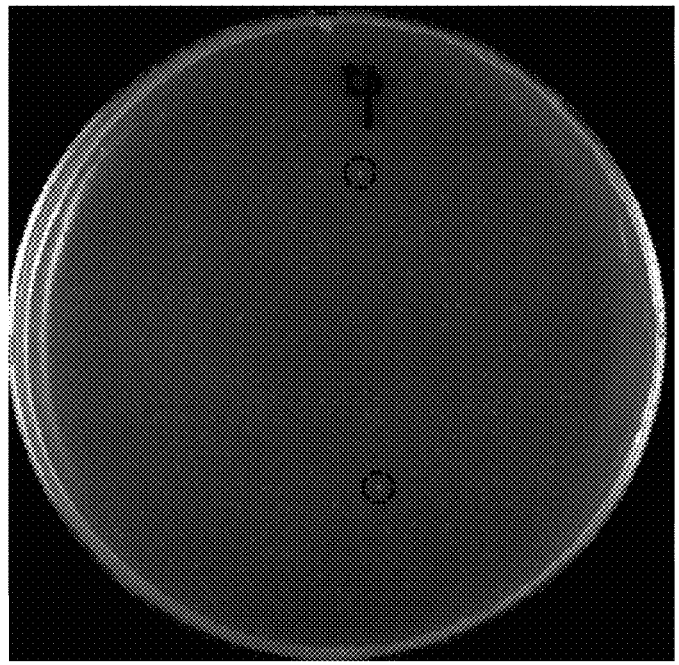

MUTANT LACTATE DEHYDROGENASE

CROSS-REFERENCE TO RELATED APPLICATION

This application claims the benefit of Korean Patent Application No. 10-2015-0075373, filed on May 28, 2015, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 44,846 Byte ASCII (Text) file named "721906_ST25_Revised.TXT," created on Aug. 8, 2016.

BACKGROUND

1. Field

The present disclosure relates to a method of screening a lactate dehydrogenase mutant, a lactate dehydrogenase mutant, a polynucleotide, a vector, a microorganism including the lactate dehydrogenase mutant, and a method of producing lactate using the microorganism.

2. Description of the Related Art

Lactate is an organic acid widely used in a variety of industrial fields, including food, pharmaceutical, chemical, and electronic industries. Lactate is a colorless, odorless, water-soluble, low-volatile compound. Lactate is not toxic to the human body and is used as a flavoring agent, a sour taste agent, a preserving agent, or the like. Additionally, lactate is used as a source for a polylactic acid (PLA) that is an environmentally friendly, biodegradable plastic known as an alternate polymeric material.

Technically, PLA is a polyester-based resin obtained by ring-opening polymerization of a dimer lactide for polymerization. PLA may be variously processed into a film, a sheet, a fiber, an injection, etc. Thus, demands for PLA as bioplastics have recently increased to replace existing general petrochemical plastics, such as polyethylene (PE), polypropylene (PP), polyethylene terephthalate (PET), or polystyrene (PS).

In addition, lactate includes both a hydroxyl group and a carboxyl group and thus is highly reactive. Accordingly, lactate can be easily converted into an industrially important compound, such as lactate ester, acetaldehyde, or propyleneglycol, and thus has received attention as an alternative chemical material of the next generation for use in the chemical industry.

Currently, lactate is produced industrially by either a petrochemical synthesis process or a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing using hydrochloric acid or sulfuric acid. The biotechnological fermentation process is used to manufacture lactate in a microorganism from a reproducible carbohydrate, such as starch, sucrose, maltose, glucose, fructose, or xylose, as a substrate.

Under this background, a lactate dehydrogenase mutant and a method of efficiently producing lactate using the lactate dehydrogenase mutant are needed.

SUMMARY

Provided is a method of screening a lactate dehydrogenase mutant having an increased lactate dehydrogenase activity, compared to the wild-type lactate dehydrogenase activity.

Provided is the lactate dehydrogenase mutant.

Provided is a polynucleotide encoding the lactate dehydrogenase mutant.

Provided is a vector including the polynucleotide encoding the lactate dehydrogenase mutant.

Provided is a microorganism including the polynucleotide encoding the lactate dehydrogenase mutant.

Provided is a method of producing lactate using the microorganism.

BRIEF DESCRIPTION OF THE DRAWINGS

These and/or other aspects will become apparent and more readily appreciated from the following description of the exemplary embodiments, taken in conjunction with the accompanying drawing in which:

FIG. 1 depicts a culture plate after culturing.

DETAILED DESCRIPTION

The term "sequence identity" of a nucleic acid or a polypeptide, as used herein, refers to a degree of identity between bases or amino acid residues of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN or BLASTP (NCBI), CLC Main Workbench (CLC bio) and MegAlign™ (DNASTAR Inc). Various levels of sequence identity may be used to identify various types of polypeptides or polynucleotides having the same or similar functions or activities. For example, the sequence identity may include a sequence identity of about 75% or more, about 80% or more, about 85% or more, about 90% or more, about 95% or more, about 96% or more, about 97% or more, about 98% or more, about 99% or more, or 100%.

The term "genetic modification", as used herein, includes a modification of introducing a polynucleotide encoding a polypeptide (e.g., an increase in a copy number of the gene), or substitution, addition, insertion, or deletion of one or nucleotides in a genetic material of a parent cell, or a chemical mutation of a genetic material of a parent cell. The genetic modification includes a coding region of a polypeptide that is heterologous, homologous, or both heterologous and homologous to a referenced species, or a functional fragment thereof. The genetic modification also includes modifications in non-coding regulatory regions that are capable of modifying expression of a gene or an operon, in which the non-coding regions include a 5'-non coding sequence and/or a 3'-non coding sequence.

The term "gene" refers to a nucleic acid fragment capable of producing an expression product, for example, mRNA or protein, by any one of transcription and translation, and may include a coding region as well as regulatory sequences such as a 5'-non coding sequence or a 3'-non coding sequence.

The term "cell", "strain", or "microorganism" may be used interchangeably and may include a yeast, a bacterium, or a fungus.

The term "parent strain" or "parent cell" refers to an original cell, for example, a non-genetically engineered cell of the same type as an engineered microorganism cell. With respect to a particular genetic modification, the "parent cell" may be a cell that lacks the particular genetic modification, but is identical in all other respects. Thus, the parent cell may be a cell that is used as a starting material to produce a genetically engineered microorganism having increased activity of a given protein.

The parent strain or parent cell may be used for a subject genetic modification. Since the parent cell may be identical to a subject cell, except for a particular genetic modification, it may be a reference cell with respect to the genetic modification. The "genetic modification" means an artificial alteration in a constitution or structure of a genetic material of a cell. The parent cell may be a cell that does not have the corresponding genetic modification, for example, genetic modification of increasing the activity.

The term "wild-type" polypeptide or polynucleotide may be a polypeptide or polynucleotide having no particular genetic modification, and the genetic modification is to obtain a genetically engineered polypeptide or polynucleotide.

The term "disruption" or "disrupting mutation" refers to a genetic modification that reduces expression of a referenced gene. The disruption includes a genetic manipulation whereby the referenced gene is not expressed (hereinafter, referred to as "inactivation" of a gene) or a genetic manipulation whereby the gene is expressed at a reduced level (hereinafter, referred to as "attenuation" of a gene). The inactivation includes not only no expression of a functional product of a gene but also expression of a non-functional product even though the gene is expressed. The attenuation includes a reduction in the expression level of a functional product of a gene. That is, the attenuation includes a reduction in the expression level of the functional product even though the entire expression of the gene is increased. Herein, the functional product of the gene refers to a product retaining a biochemical or physiological function (e.g., enzymatic activity) of the product (e.g., enzyme) of the gene in a parent cell or a wild-type cell. Thus, the disruption includes functional disruption of the gene. The genetic modifications include a modification of introducing a polynucleotide encoding a polypeptide, a substitution, addition, insertion, or deletion of one or more nucleotides with respect to a genetic material of a parent cell, or a chemical modification of the genetic material of the parent cell. Such genetic modifications include genetic modifications in coding regions and functional fragments thereof for heterologous, homologous, or both heterologous and homologous polypeptides for the referenced species. In addition, the genetic modifications include modifications of non-coding regulatory regions, which alter the expression of a gene or an operon. The non-coding regions include a 5'-non coding sequence and/or a 3'-non coding sequence.

The disruption of a gene may be achieved by genetic manipulation such as homologous recombination, directed mutagenesis, or molecular evolution. If a cell includes a plurality of the same genes, or two or more different paralogs of a gene, one or more of the genes may be disrupted. For example, the genetic modification may be performed by transforming the cell with a vector containing a partial sequence of the gene, culturing the cell so that the gene is disrupted by homogenous recombination of the sequence with an endogenous gene of the cell, and then selecting cells, in which the homologous recombination occurred, using a selection marker.

The term "gene", as used herein, refers to a nucleic acid fragment expressing a specific protein, and may include or not a regulatory sequence of a 5'-non coding sequence and/or a 3'-non coding sequence.

As used herein, the term "exogenous" means that a referenced molecule or a referenced activity is introduced into a host cell. The molecule may be introduced, for example, by introducing a coding nucleic acid into a genetic material of the host, such as integration into a host chromosome, or as a non-chromosomal genetic material such as a plasmid. The term "exogenous", when used in reference to expression of a coding nucleic acid, refers to introduction of the coding nucleic acid in an expressible form into an individual. The term "exogenous", when used in reference to biosynthetic activity, refers to activity that is introduced into a host parent cell. The source may be, for example, a homologous or heterologous coding nucleic acid that expresses the referenced activity following introduction into the host parent cell. Therefore, the term "endogenous" refers to a referenced molecule or activity that is already present in the host cell before a particular genetic manipulation. Similarly, the term "endogenous", when used in reference to expression of a coding nucleic acid, refers to expression of a coding nucleic acid previously contained in a subject before a given genetic manipulation. The term "heterologous" refers to a molecule or activity derived from a source other than the referenced species, whereas "homologous" refers to a molecule or activity derived from the same species as the host parent cell. Accordingly, exogenous expression of a coding nucleic acid may utilize either or both of heterologous and homologous coding nucleic acids.

The term "genetic engineering" or "genetically engineered", as used herein, refers to action of introducing one or more genetic modifications into a cell or a cell produced thereby.

The term "lactate", as used herein, includes "lactic acid" itself as well as a negative ion, a salt, solvate, or polymorph thereof, or a combination thereof. The salt may be, for example, an inorganic acid salt, an organic acid salt, or a metal salt. The inorganic acid salt may be hydrochloride, bromate, phosphate, sulfate or disulfate. The organic acid salt may be formate, acetate, propionate, lactate, oxalate, tartrate, malate, maleate, citrate, fumarate, besylate, camsylate, edisilate, trifluoroacetate, benzoate, gluconate, methanesulfonate, glycolate, succinate, 4-toluenesulfonate, galacturonate, embonate, glutamate or aspartate. The metal salt may be a calcium salt, a sodium salt, a magnesium salt, a strontium salt or a potassium salt.

An aspect provides a method of screening a microorganism having a mutant lactate dehydrogenase with increased activity, the method comprising: preparing a nucleic acid encoding a mutant lactate dehydrogenase; introducing the nucleic acid encoding the mutant lactate dehydrogenase into a genetically engineered microorganism having a NADH consumption rate lower than a wild-type microorganism, to obtain the microorganisms having the nucleic acid; culturing the microorganisms having the nucleic acid; and determining the microorganism having an higher growth rate among the microorganisms having the nucleic acid, as a microorganism having a mutant lactate dehydrogenase with increased activity.

The lactate dehydrogenase may be D-lactate dehydrogenase.

The method of screening a microorganism having a mutant lactate dehydrogenase with increased activity may include preparing a nucleic acid encoding a mutant lactate dehydrogenase.

The mutant may be prepared by mutagenesis of a gene encoding the wild-type lactate dehydrogenase. The gene encoding the wild-type lactate dehydrogenase may be derived from *Lactobacillus bulgaricus*. The mutagenesis may be one or more selected from random mutagenesis, directed mutagenesis, DNA shuffling, and point mutagenesis. The directed mutagenesis may include site-directed mutagenesis.

The random mutagenesis may be error-prone PCR. The random mutagenesis may be carried out using a PCR mutagenesis kit known in the art. When mutagenesis by error-prone PCR is performed, different mutants may be selectively prepared by controlling one or more conditions selected from the amount of a template, the ratio of dNTP, and the type of DNA polymerase.

The method of screening a microorganism having a mutant lactate dehydrogenase with increased activity may include introducing the nucleic acid encoding the mutant lactate dehydrogenase into a genetically engineered microorganism having a NADH consumption rate lower than a wild-type microorganism, to obtain the microorganisms having the nucleic acid.

The genetically engineered microorganism may be a microorganism having decreased activity, compared to its parent strain or a wild-type microorganism, of one or more selected from a polypeptide converting fumarate to succinate, a polypeptide converting pyruvate to D-lactate, and a polypeptide converting acetyl-CoA to ethanol. The genetically engineered microorganism may have genetic modifications disrupting one or more genes selected from the group consisting of a gene encoding the polypeptide that converts fumarate to succinate, a gene encoding the polypeptide that converts pyruvate to D-lactate, and a gene encoding the polypeptide that converts acetyl-CoA to ethanol. This disruption is the same as in the above description of the term "disruption". The polypeptide that converts fumarate to succinate may be fumarate reductase classified as EC 1.3.1.6. The polypeptide that converts pyruvate to D-lactate may be D-lactate dehydrogenase classified as EC 1.1.1.28. The polypeptide that converts acetyl-CoA to ethanol classified as EC 1.1.1.1. The genetically engineered microorganism may be *Escherichia coli*.

The introduction of the nucleic acid encoding the mutant into a genetically engineered microorganism may be carried out by transformation. The term "transformation", as used herein, means introduction of DNA into a host cell so that the DNA is replicable, either as an extrachromosomal element or by chromosomal integration. The introduction of the nucleic acid may be achieved through a plasmid. A general transformation method may be, for example, a DEAE-dextran or calcium phosphate method, microinjection, a DNA-containing liposome method, a lipofectamine-DNA complex method, or electroporation. The cell line, that is, the host cell may be animal cells, *E. coli* cells (e.g., DH5a competent cells), BHK cells, CHO cells, COS cells or cancer cells. The transformation method is known in the art.

The method of screening a microorganism having a mutant lactate dehydrogenase with increased activity may include culturing the microorganisms having the nucleic acid; and determining (e.g., selecting) the microorganism having an higher growth rate among the microorganisms having the nucleic acid, as a microorganism having a mutant lactate dehydrogenase with increased activity.

The culturing may be performed under a microaerobic condition or an anaerobic condition. The microorganisms may be cultured under the same conditions for a predetermined time. Then, the growth rates of the microorganisms which have been cultured under the same conditions for a predetermined time may be compared to determine the microorganism having an higher growth rate among the microorganisms.

The mutant lactate dehydrogenase with increased activity may have a higher consumption rate of NADH compared to the wild-type lactate dehydrogenase. The mutant lactate dehydrogenase with increased activity may have a higher affinity to pyruvate compared to the wild-type lactate dehydrogenase. The activity may be specific activity. The consumption rate of NADH may be identified by one or more of Km for NADH and kcat for NADH. The consumption rate of NADH may be measured using a kit for lactate dehydrogenase assay (e.g., Lactate Dehydrogenase Activity Assay Kit (cat. #K726-500, BioVision)). The affinity of the lactate dehydrogenase to pyruvate may be identified by one or more of Km for pyruvate and kcat for pyruvate.

Another aspect of the disclosure provides a lactate dehydrogenase mutant polypeptide and nucleic acid encoding same.

The mutant may have an amino acid sequence prepared by substituting the 15th and/or 329th amino acid of SEQ ID NO: 1 with a different amino acid. Lactate dehydrogenase having the amino acid sequence of SEQ ID NO: 1 may be derived from *Escherichia coli* (*E. Coli*). The amino acid substituted at position 15 and/or 329 of SEQ ID NO: 1 may be a polar, uncharged amino acid. Examples of such amino acids include serine, glutamine, asparagine, threonine, or cysteine. The mutant may have a substitution of serine(S) for the $15^{th}$ amino acid, proline (P) in SEQ ID NO: 1. Alternatively, or in addition, the mutant may have a substitution of glutamine (Q) for the $329^{th}$ amino acid, proline (P) in SEQ ID NO: 1. The mutant having a substitution of serine (S) for the $15^{th}$ amino acid in SEQ ID NO: 1 may have an amino acid sequence of SEQ ID NO: 3. The mutant having a substitution of glutamine (Q) for the $329^{th}$ amino acid in SEQ ID NO: 1 may have an amino acid sequence of SEQ ID NO: 5.

The lactate dehydrogenase (LDH) may be an enzyme that catalyzes conversion of pyruvate to lactate. The LDH may be an enzyme producing D-lactate, classified as EC 1.1.1.28, or an enzyme producing L-lactate, classified as EC 1.1.1.27.

The D-lactate dehydrogenase (D-LDH) may be an enzyme classified as EC 1.1.1.28. The D-LDH may be also referred to as D-specific 2-hydroxyacid dehydrogenase. The D-LDH may be an enzyme that catalyzes conversion of pyruvate and NADH into (R)-lactate and $NAD^+$.

The L-lactate dehydrogenase (L-LDH) may be an enzyme classified as EC 1.1.1.27. The L-LDH may be also referred to as L-specific 2-hydroxyacid dehydrogenase. The L-LDH may be an enzyme that catalyzes conversion of pyruvate and NADH into (S)-lactate and $NAD^+$.

The lactate dehydrogenase mutant may have an improved specific activity, compared to that of the wild-type or non-modified lactate dehydrogenase. The specific activity of the lactate dehydrogenase may be about 10% to 100%, about 15% to 50%, about 20% to 40%, or about 25% to 30% higher than that of the wild-type or non-modified lactate dehydrogenase.

Still another aspect of the disclosure provides a polynucleotide encoding the mutant lactate dehydrogenase.

The term "polynucleotide" encompasses DNA molecules such as gDNA and cDNA, and RNA molecules, and a nucleotide constituting the polynucleotide may include natural nucleotides as well as analogues that are modified in the sugar or base moieties. The polynucleotide may be an isolated polynucleotide.

Still another aspect provides a vector or an expression cassette including the polynucleotide encoding the lactate dehydrogenase. In the vector or expression cassette, the polynucleotide may be operably linked to a regulatory sequence. The cassette may be a unit sequence capable of expressing a protein from the polynucleotide operably linked to the regulatory sequence. The "operably linked" means a functional linkage between the nucleic acid expression regulatory sequence and another nucleotide sequence. This linkage allows the regulatory sequence to control transcription and/or translation of the nucleotide sequence of the gene. The regulatory sequence may include a replication origin, a promoter, a terminator, and/or an enhancer. The promoter may be also operably linked to a sequence encoding a gene. The promoter may be one or more promoters selected from the promoters derived from covalently linked cell wall protein 12 (CCW12), glyceraldehyde-3-phosphate dehydrogenase (GPD), pyruvate decarboxylase 1 (PDC1), phosphoglycerate kinase (PGK), transcription enhancer factor 1 (TEF1), glyceraldehyde-3-phosphate dehydrogenase (TDH), triose phosphate isomerase (TPI), purine-cytosine permease (PCPL3), and alcohol dehydrogenase (ADH) genes. The CCW12 promoter, CYC promoter, TEF1 promoter, PGK1 promoter, GPD promoter, and ADH promoter may have a nucleotide sequence of SEQ ID NO: 11, 12, 13, 14, 15, and 16, respectively. The terminator may be selected from the group consisting of PGK1 (phosphoglycerate kinase 1), CYC1 (cytochrome c transcription), and GAL1. The CYC1 terminator may have a nucleotide sequence of SEQ ID NO: 17. The vector may further include a selection marker. The selection marker may be ura3 (orotidine-5'-phosphate decarboxylase).

Still another aspect provides a microorganism including the polynucleotide or vector encoding lactate dehydrogenase mutant.

The microorganism may include micro-sized prokaryotes, eukaryotes, or organisms. The microorganism may include archaeabacteria; eubacteria; or eukaryotic microorganisms such as yeast and fungus. The microorganism may be a microorganism belonging to the genus Escherichia. The microorganism may be E. coli.

All other aspects of the lactate dehydrogenase mutant are the same as described above.

The polynucleotide encoding the lactate dehydrogenase mutant may be an exogenous gene. The microorganism may have an expression cassette or a vector that includes the exogenous gene encoding the mutant. The microorganism may include the exogenous gene that is introduced into a parent cell by a vector, for example, an expression vector. The microorganism may include the exogenous gene that is introduced in the form of a linear polynucleotide, for example, an expression cassette into the parent cell. The exogenous gene may be expressed from the expression vector, for example, a plasmid within the cell. For stable expression, the exogenous gene may be expressed by integration into a genetic material, for example, chromosome within the cell.

The microorganism may express the above described lactate dehydrogenase mutant. The microorganism may show an increase in the activity to convert pyruvate to lactate, compared to its parent strain.

The term "increase in activity" or "increased activity", as used herein, may refer to a detectable increase in an activity of a cell, a protein, or an enzyme. The "increase in activity" or "increased activity" may also refer to an activity level of a modified (e.g., genetically engineered) cell, protein, or enzyme that is higher than that of a comparative cell, protein, or enzyme of the same type, such as a cell, protein, or enzyme that does not have a given genetic modification (e.g., original or "wild-type" cell, protein, or enzyme). The "cell activity" may refer to an activity of a particular protein or enzyme of a cell. For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more than an activity of a non-engineered cell, protein, or enzyme of the same type, i.e., a wild-type cell, protein, or enzyme. An activity of a particular protein or enzyme in a cell may be increased by about 5% or more, about 10% or more, about 15% or more, about 20% or more, about 30% or more, about 50% or more, about 60% or more, about 70% or more, or about 100% or more than an activity of the same protein or enzyme in a parent cell, e.g., a non-engineered cell. A cell having an increased activity of a protein or an enzyme may be identified by using any method known in the art. The cell having the increased activity may have one or more genetic modifications of increasing the activity of the enzyme or polypeptide, compared to a cell having no genetic modification.

The microorganism may include a non-natural microorganism. The term "non-natural" microorganism refers to a microorganism having one or more genetic modifications that are not generally found in the natural strain of the referenced species including the wild-type strain of the referenced species. The genetic modifications may include, for example, introduction of a polynucleotide encoding a polypeptide, addition of other polynucleotides, deletion of polynucleotides, and/or disruption of the genetic material of the yeast cell. The genetic modifications may include, for example, coding regions and functional fragments thereof for heterologous, homologous, or both heterologous and homologous polypeptides for the referenced species. Additional modification may include, for example, modifications in non-coding regulatory regions that are capable of modifying expression of a gene or an operon. For example, the microorganism may have an exogenous gene encoding the lactate dehydrogenase mutant and a genetic modification of decreasing activity of an NADH consuming pathway. The NADH consuming pathway may be a pathway of producing succinate from PEP, a pathway of producing D-lactate from pyruvate, a pathway of producing ethanol from acetyl-CoA, or a combination thereof. An enzyme involved in the pathway of producing succinate from PEP may be fumarate reductase. An enzyme involved in the pathway of producing D-lactate from pyruvate may be D-lactate dehydrogenase. An enzyme involved in the pathway of producing ethanol from acetyl-CoA may be alcohol dehydrogenase.

The microorganism may have a decreased activity of a pathway of preventing a flow of a metabolite to lactate, compared to its parent strain. The term "decrease in activity"

or "decreased activity", as used herein, means that a cell has an activity of an enzyme or a polypeptide being lower than that measured in a parent cell (e.g., a non-genetically engineered cell of the same type). Also, the "decrease in activity" or "decreased activity" means that an isolated enzyme or a polypeptide has an activity being lower than that of an original or a wild-type enzyme or polypeptide. The decrease in activity or decreased activity encompasses no activity. For example, a modified (e.g., genetically engineered) cell or enzyme has enzymatic activity of converting a substrate to a product, which shows about 20% or more, about 30% or more, about 40% or more, about 50% or more, about 55% or more, about 60% or more, about 70% or more, about 75% or more, about 80% or more, about 85% or more, about 90% or more, about 95% or more, or about 100% decrease, compared to that of a cell or enzyme that does not have the modification, i.e., a parent cell or a "wild-type" cell or enzyme. Decreased activity of an enzyme or a cell may be confirmed by any methods known in the art. The decrease in activity includes the case that an enzyme has no activity or decreased activity even though the enzyme is expressed, or the case that an enzyme-encoding gene is not expressed or expressed at a low level, compared to a cell having a non-modified gene, i.e., a parent cell or a wild-type cell. The cell having decreased activity may have one or more genetic modifications of decreasing the activity of the enzyme or polypeptide, compared to a cell having no genetic modification.

The microorganism may have decreased activity of one or more selected from a polypeptide converting fumarate to succinate, a polypeptide converting pyruvate to D-lactate, and a polypeptide converting acetyl-CoA to ethanol, compared to its parent strain.

The polypeptide converting fumarate to succinate may be fumarate reductase. the fumarate reductase may catalyze the following reaction:

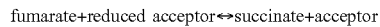

fumarate+reduced acceptor↔succinate+acceptor

The fumarate reductase may be an enzyme classified as EC 1.3.1.6. The fumarate reductase may include four subunits of subunit A, subunit B, subunit C, and subunit D. The fumarate reductase subunit A is a polypeptide that converts fumarate to succinate and has an amino acid sequence of SEQ ID NO: 7. A gene encoding the amino acid may have a polynucleotide sequence of SEQ ID NO: 8.

The polypeptide converting pyruvate to D-lactate may be D-lactate dehydrogenase. The D-lactate dehydrogenase is the same as described above.

The polypeptide converting acetyl-CoA to ethanol may be alcohol dehydrogenase (Adh). The alcohol dehydrogenase may be an enzyme that catalyzes reversible conversion of acetyl CoA to ethanol with oxidation of NADH to $NAD^+$. The alcohol dehydrogenase may be an enzyme classified as EC.1.1.1.1. The polypeptide converting acetyl CoA to ethanol may have an amino acid sequence of SEQ ID NO: 9. A gene encoding the polypeptide may have Gene ID of 12753141 in EcoGene-RefSeq. The gene may be *E. Coli* adhE encoding NADH-linked alcohol dehydrogenase. The adhE gene may have a nucleotide sequence of SEQ ID NO: 10.

Still another aspect provides a method of producing lactate including culturing the microorganism. The microorganism is the same as described above.

The culture may be performed in a medium containing a carbon source, for example, glucose. The medium used for culturing the yeast cell may be any general medium that is suitable for host cell growth, such as a minimal or complex medium containing proper supplements. The suitable medium may be commercially available or prepared by a known preparation method. The medium used for the culture may be a medium that satisfies the requirements of a particular yeast cell. The medium may be a medium selected from the group consisting of a carbon source, a nitrogen source, a salt, trace elements and combinations thereof.

The culture conditions may be properly controlled in order to obtain lactate from the genetically engineered yeast cell. For proliferation, the cell may be cultured under aerobic conditions. Thereafter, the cell may be cultured under microaerobic conditions or anaerobic conditions in order to produce lactate. The term "anaerobic conditions" means oxygen deficient conditions. The term "microaerobic conditions", when used in reference to culture or growth conditions, means that a concentration of dissolved oxygen (DO) in a medium is more than 0% and less than about 10% of saturation for DO in a liquid medium. The microaerobic conditions also include growing or resting cells in a liquid medium or on a solid agar plate inside a sealed chamber which is maintained with an atmosphere of less than 1% oxygen. The percentage of oxygen may be maintained by, for example, sparging the culture with an $N_2/CO_2$ mixture or other suitable non-oxygen gas. The oxygen conditions include maintaining the concentration of DO at 0% to 10%, for example, 0 to 8%, 0 to 6%, 0 to 4%, or 0 to 2%.

The term "culture conditions" means conditions for culturing the yeast cell. Such culture conditions may include, for example, a carbon source, a nitrogen source, or an oxygen condition utilized by the yeast cell. The carbon source that may be utilized by the yeast cell may include monosaccharides, disaccharides, or polysaccharides. The carbon source may be glucose, fructose, mannose, or galactose. The nitrogen source that may be utilized by the yeast cell may be an organic nitrogen compound or an inorganic nitrogen compound. The nitrogen source may be exemplified by amino acids, amides, amines, nitrates, or ammonium salts.

The method of producing lactate may further include collecting lactate from the culture.

Collecting lactate from the culture may be performed by isolation using a general method known in the art. Such isolation method may be centrifugation, filtration, ion chromatography, or crystallization. For example, the culture is centrifuged at a low speed to remove biomass, and a resulting supernatant is subjected to ion chromatography for isolation.

The method of screening a lactate dehydrogenase mutant according an aspect may be used to obtain a lactate dehydrogenase mutant having increased activity, compared to the wild-type lactate dehydrogenase.

The lactate dehydrogenase mutant according an aspect may have increased activity, compared to the wild-type lactate dehydrogenase, thereby being used for efficient production of lactate.

The polynucleotide encoding the lactate dehydrogenase mutant, the vector and the mutant according an aspect may have increased lactate dehydrogenase activity, compared to the wild-type lactate dehydrogenase activity, thereby being used for efficient production of lactate.

The method of producing lactate using the mutant according to an aspect may be used to efficiently produce lactate.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to the exemplary embodiments. However, the exemplary embodiments described herein should be considered in a descriptive sense only and not for purposes of limitation.

Example 1. Preparation of Lactate Dehydrogenase Mutant

PCR is performed using 100 ng of wild-type D-ldh DNA from *Lactobacillus bulgaricus* as a template and a primer set of SEQ ID NOS: 18 and 19 as primers to amplify a wild-type D-ldh gene of SEQ ID NO: 2.

50 μl of a PCR reaction mixture is prepared as follows:

42.5 μl of water containing 100 ng of the amplified wild-type D-ldh gene, 5 μl of 10× Mutazyme II reaction buffer, 1 μl of 40 mM dNTP mix (final concentration of each dNTP is 200 μM), 0.5 μl of a primer mix of SEQ ID NOS: 18 and 19 (concentration of each primer is 250 ng/μl), and 1 μl of 2.5 U/μl Mutazyme II DNA polymerase.

The reagents are placed in a temperature cycler, and PCR is performed at 95° C. for 2 minutes (95° C. for 30 seconds, 58° C. for 30 seconds, 72° C. for 1 minute)×25 cycles, and then at 72° C. for 10 minutes. The above described PCR is error-prone PCR, and a GeneMorph II random mutagenesis kit (Agilent) is used. As a result, a D-ldh mutant gene is obtained.

Example 2. Preparation of *E. Coli* K12 Δ ldhA Δ adhE Δ frdAB 2.1 Deletion of ldhA, adhE, and frdAB Genes ldhA, adhE, and frdAB genes are deleted in *E. coli* K12 using a one-step inactivation method [Warner et al., PNAS, 6; 97(12):6640-6645, 2000; lee, K. H. et al., Molecular systems biology 3, 149, 2007].

To delete the ldhA gene, PCR is performed using a pMloxC vector [lee, K. H. et al., Molecular systems biology 3, 149 (2007)] as a template and primers of SEQ ID NOS: 20 and 21. A DNA fragment thus obtained is electroporated into competent cells of *E. coli* K12 strain expressing λ Red recombinase so as to prepare a ldhA-deleted mutant strain, *E. coli* K12 Δ ldhA.

To delete the adhE gene, a PCR fragment that is obtained using primers of SEQ ID NOS: 22 and 23 in the same manner as above is introduced into *E. coli* K12 Δ ldhA so as to prepare an adhE-deleted mutant strain, *E. coli* K12 Δ ldhA ΔadhE.

To delete the frdAB gene, a PCR fragment that is obtained using primers of SEQ ID NOS: 24 and 25 in the same manner as above is introduced into *E. coli* K12 Δ ldhA Δ adhE so as to prepare a frdAB-deleted mutant strain, *E. coli* K12 Δ ldhA Δ adhE Δ frdAB.

Example 3. Introduction and Selection of Lactate Dehydrogenase Mutant

The D-ldh mutant gene (ldhM) obtained in Example 1 is introduced into a pT7R3H vector. The pT7R3H vector has a nucleotide sequence of SEQ ID NO: 26. The obtained D-ldh mutant gene and pT7R3H vector, and an in-fusion HD cloning kit (Clontech) are used to prepare a pT7R3H-ldhM vector.

The pT7R3H-ldhM vector thus prepared is introduced into *E. coli* K12 Δ ldhA Δ adhE Δ frdAB prepared in Example 2 by a heat shock method (Sambrook, J & Russell, D. W., New York: Cold Spring Harbor Laboratory Press, 2001). The transformed strain is cultured on a plate containing an M9 minimal medium under microaerobic conditions at 37° C. for 24 hours. The M9 medium is prepared as follows: M9 salts are prepared. Then, to prepare M9 salt aliquots, 800 ml of $H_2O$ and 64 g of $Na_2HPO_4$-$7H_2O$, 15 g of $KH_2PO_4$, 2.5 g of NaCl, and 5.0 g of $NH_4Cl$ are added and stirred until they are dissolved. Thereafter, distilled water is added to the M9 salt aliquot to adjust the volume to 1,000 ml, followed by sterilization in an autoclave. Then, 200 ml of the M9 salt aliquot is added to about 700 ml of sterile distilled water. 2 ml of sterile 1M $MgSO_4$ and 20 ml of 20% glucose are added to the mixture, and then distilled water is added thereto so as to prepare 1,000 ml of M9 medium.

FIG. 1 is a photograph of a plate after culturing. As shown in FIG. 1, two colonies are observed. These colonies are those that grow rapidly under the culture conditions, indicating a high growth rate.

Plasmid DNAs are isolated from the two colonies, followed by sequencing analysis. The genes are identified to have a sequence of SEQ ID NO: 4 and SEQ ID NO: 6, respectively. Amino acid sequences thereof are examined, and thus they are identified to have SEQ ID NO: 3 and SEQ ID NO: 5. A mutant having the amino acid sequence of SEQ ID NO: 3 is designated as mut1 and a mutant having the amino acid sequence of SEQ ID NO: 5 is designated as mut2.

Example 4. Test of Activity of Selected Lactate Dehydrogenase Mutant

The mutant amino acid identified in Example 3 is subjected to ldh assay as follows. In detail, 20 μl of 1M pyruvate and 10 μl of 10 mM NADH are added to 1 ml of 50 mM potassium phosphate buffer at pH 8.0. 5 ul of 1 ng/μl ldh mutant (mut1 or mut2) is added to this buffer, and NADH reduction is measured for 2 minutes. Further, the wild-type ldh is also subjected to ldh assay of performed in the same manner as above.

In Table 1, specific activity, Km, and kcat for the wild-type or mutant lactate dehydrogenase are given, based on the measured values. As shown in Table 1, the mutants, mut1 and mut2 exhibit increased kcat for NADH, compared to the wild-type ldh, indicating that the respective mutants have increased NADH consumption rate, and activities of the mutants are increased. Further, the mutants, mut1 and mut2 exhibit decreased Km for pyruvate, indicating that the respective mutants have increased affinity for the substrate pyruvate.

TABLE 1

|  | Specific activity (U/mg) | Km (mM) for NADH | kcat for NADH | Kcat/Km for NADH | Km (mM) for pyruvate | kcat for pyruvate | kcat/Km for pyruvate |
|---|---|---|---|---|---|---|---|
| Wild-type ldh | 1824.9 | 0.387 | $1.41 \times 10^7$ | $3.66 \times 10^7$ | 2.326 | $1.74 \times 10^7$ | $0.75 \times 10^7$ |
| Mut1 ($P^{15}S$) | 1669.6 | 0.529 | $1.68 \times 10^7$ | $3.18 \times 10^7$ | 1.010 | $1.38 \times 10^7$ | $1.37 \times 10^7$ |
| Mut2 ($P^{329}Q$) | 2313.8 | 1.207 | $3.52 \times 10^7$ | $3.42 \times 10^7$ | 1.546 | $1.74 \times 10^7$ | $1.13 \times 10^7$ |

Example 5. Test of Sugar Consumption, D-Lactate Production, and Cell Growth of Microorganism Including Lactate Dehydrogenase Mutant The wild-type ldh, and the mutants, mut1 and mut2 are introduced into *E. coli* K12 Δ ldhA Δ adhE Δ frdAB strain prepared in Example 2 by a heat shock method, respectively (Sambrook, J & Russell, D. W., New York: Cold Spring Harbor Laboratory Press, 2001). The respective transformed strains are inoculated in a 125 ml-flat-cap flask containing 20 ml of a glucose minimal medium, and cultured under microaerobic conditions at 37° C. for 6 hours. The initial glucose amount is 17.2 g/L. After culture, $OD_{600}$ values are measured using a spectrophotometer. Concentrations of glucose and D-lactate are analyzed by HPLC (High performance liquid chromatography).

As shown in the following Table 2, *E. coli* including mut1 or mut2 ldh exhibits increased sugar consumption, D-LA production, production yield, and cell growth, compared to *E. coli* including the wild-type ldh.

TABLE 2

|  | Glucose consumption (g/L) | Concentration of D-lactate produced (g/L) | D-lactate production yield (%) | $OD_{600}$ |
|---|---|---|---|---|
| No ldh | 1.81 | 0.00 | 0.00 | 2.11 |
| Wild-type ldh | 2.09 | 0.40 | 19.11 | 2.05 |
| Mut1($P^{15}S$) | 2.78 | 1.10 | 39.65 | 2.54 |
| Mut2($P^{329}Q$) | 2.73 | 1.40 | 51.41 | 2.13 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A mutant lactate dehydrogenase comprising an amino acid sequence of SEQ ID NO: 1 in which the 15$^{th}$ amino acid proline (P), the 329$^{th}$ amino acid proline (P), or both, are substituted with a polar, uncharged amino acid, wherein the mutant lactate dehydrogenase has lactate dehydrogenase activity.

2. The mutant lactate dehydrogenase of claim 1, wherein the 15$^{th}$ amino acid proline (P), the 329$^{th}$ amino acid proline (P), or both, in SEQ ID NO: 1 is substituted with serine, glutamine, asparagine, threonine, or cysteine.

3. The mutant lactate dehydrogenase of claim 1, wherein the mutant lactate dehydrogenase comprises SEQ ID NO: 3 or 5.

* * * * *

SEQUENCE LISTING

<160> NUMBER OF SEQ ID NOS: 26

<210> SEQ ID NO 1
<211> LENGTH: 333
<212> TYPE: PRT
<213> ORGANISM: Escherichia coli

<400> SEQUENCE: 1

Met Thr Lys Ile Phe Ala Tyr Ala Ile Arg Glu Asp Glu Lys Pro Phe
1               5                   10                  15

Leu Lys Glu Trp Glu Asp Ala His Lys Asp Val Glu Val Glu Tyr Thr
            20                  25                  30

Asp Lys Leu Leu Thr Pro Glu Thr Ala Ala Leu Ala Lys Gly Ala Asp
            35                  40                  45

Gly Val Val Tyr Gln Gln Leu Asp Tyr Thr Ala Glu Thr Leu Gln
 50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                 85                  90                  95

Thr Asn Val Pro Val Tyr Ser Pro Asn Ala Ile Ala Glu His Ala Ala
                100                 105                 110

Ile Gln Ala Ala Arg Ile Leu Arg Gln Ala Lys Ala Met Asp Glu Lys
            115                 120                 125

Val Ala Arg His Asp Leu Arg Trp Ala Pro Thr Ile Gly Arg Glu Val
130                 135                 140

Arg Asp Gln Val Val Gly Val Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
                180                 185                 190

Leu Asp Asp Leu Tyr Lys Gln Ala Asp Val Ile Ser Leu His Val Pro
195                 200                 205

Asp Val Pro Ala Asn Val His Met Ile Asn Asp Lys Ser Ile Ala Lys
            210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
                260                 265                 270

Trp Glu Gly Lys Glu Phe Pro Asp Ala Arg Leu Ala Asp Leu Ile Ala
            275                 280                 285

Arg Pro Asn Val Leu Val Thr Pro His Thr Ala Phe Tyr Thr Thr His
290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Pro Val Lys Val Gly
                325                 330

<210> SEQ ID NO 2
<211> LENGTH: 1002
<212> TYPE: DNA
<213> ORGANISM: Escherichia coli

<400> SEQUENCE: 2
atgactaaaa tcttcgctta cgctataaga gaggacgaaa agccattttt gaaagagtgg     60
gaggatgcgc ataaagatgt tgaagttgag tacacggata aacttttaac tcctgaaact    120
gctgcattgg caaagggtgc agacggcgta gtagtatatc aacagcttga ttatacagct    180
gaaaccctcc aagctctcgc tgataatggg attacaaaaa tgtctttgcg taatgtaggt    240
gttgacaaca tagacatggc caaagcaaag gaactaggct ttcaaatcac aaatgtgcct    300
gtgtactcac caaatgctat cgctgaacac gctgccatac aagccgctag aatcttaaga    360
caggcgaagg ctatggatga aaaggttgca agacatgatc taagatgggc tcctactatc    420

```
ggtagggaag taagagatca agttgtcggt gtggtgggaa caggacatat tggccaagtt      480
ttcatgcaga ttatggaagg attcggggca aaagtcattg cctacgacat ttttcgaaac      540
cctgagctgg agaaaaaggg ttactacgtt gattctctgg atgacctata caaacaagca      600
gatgttattt ctcttcatgt gccagatgtc ccagcaaatg tccacatgat caacgacaaa      660
tcaattgcca agatgaaaca agatgtcgta atcgttaatg tgagtagagg gcctttggtt      720
gacaccgacg ctgttataag gggtttggat tccggtaaag tatttggata tgcgatggat      780
gtttacgaag gtgaagtcgg tgtctttaac gaagattggg aaggcaaaga gttcccagac      840
gcaagattag ccgatttgat cgcaagacca aatgttttag taacaccaca cactgccttc      900
tatacaacac atgccgtgag aaacatggtt attaaggcat tgataataa cttagaattg       960 atcgaaggca aggaagctga aactccagtt aaggtcggtt aa                        1002
```

<210> SEQ ID NO 3
<211> LENGTH: 333
<212> TYPE: PRT
<213> ORGANISM: Artificial Sequence
<220> FEATURE:
<223> OTHER INFORMATION: Synthetic d-ldh mutation 1

<400> SEQUENCE: 3

```
Met Thr Lys Ile Phe Ala Tyr Ala Ile Arg Glu Asp Glu Lys Ser Phe
  1               5                  10                  15

Leu Lys Glu Trp Glu Asp Ala His Lys Asp Val Glu Val Glu Tyr Thr
             20                  25                  30

Asp Lys Leu Leu Thr Pro Glu Thr Ala Ala Leu Ala Lys Gly Ala Asp
         35                  40                  45

Gly Val Val Val Tyr Gln Gln Leu Asp Tyr Thr Ala Glu Thr Leu Gln
     50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                 85                  90                  95

Thr Asn Val Pro Val Tyr Ser Pro Asn Ala Ile Ala Glu His Ala Ala
            100                 105                 110

Ile Gln Ala Ala Arg Ile Leu Arg Gln Ala Lys Ala Met Asp Glu Lys
        115                 120                 125

Val Ala Arg His Asp Leu Arg Trp Ala Pro Thr Ile Gly Arg Glu Val
    130                 135                 140

Arg Asp Gln Val Val Gly Val Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
```

```
                260             265             270
Trp Glu Gly Lys Glu Phe Pro Asp Ala Arg Leu Ala Asp Leu Ile Ala
            275                 280                 285

Arg Pro Asn Val Leu Val Thr Pro His Thr Ala Phe Tyr Thr Thr His
        290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Pro Val Lys Val Gly
            325                 330

<210> SEQ ID NO 4
<211> LENGTH: 1002
<212> TYPE: DNA
<213> ORGANISM: Artificial Sequence
<220> FEATURE:
<223> OTHER INFORMATION: Synthetic d-ldh mutation 1

<400> SEQUENCE: 4
atgactaaaa tcttcgctta cgctataaga gaggacgaaa agtcattttt gaaagagtgg      60
gaggatgcgc ataaagatgt tgaagttgag tacacggata aacttttaac tcctgaaact     120
gctgcattgg caaagggtgc agacggcgta gtagtatatc aacagcttga ttatacagct     180
gaaaccctcc aagctctcgc tgataatggg attacaaaaa tgtctttgcg taatgtaggt     240
gttgacaaca tagacatggc caaagcaaag gaactaggct ttcaaatcac aaatgtgcct     300
gtgtactcac aaaatgctat cgctgaacac gctgccatac aagccgctag aatcttaaga     360
caggcgaagg ctatggatga aaaggttgca agacatgatc taagatgggc tcctactatc     420
ggtagggaag taagagatca agttgtcggt gtggtgggaa caggacatat tggccaagtt     480
ttcatgcaga ttatggaagg attcgggca aaagtcattg cctacgacat ttttcgaaac     540
cctgagctgg agaaaaaggg ttactacgtt gattctctgg atgacctata caacaagca     600 gatgttattt ctcttcatgt gccagatgtc ccagcaaatg tccacatgat caacgacaaa     660
tcaattgcca agatgaaaca agatgtcgta atcgttaatg tgagtagagg gcctttggtt     720
gacaccgacg ctgttataag gggtttggat tccggtaaag tatttggata tgcgatggat     780
gtttacgaag gtgaagtcgg tgtctttaac gaagattggg aaggcaaaga gttcccagac     840
gcaagattag ccgatttgat cgcaagacca aatgttttag taacaccaca cactgccttc     900
tatacaacac atgccgtgag aaacatggtt attaaggcat ttgataataa cttagaattg     960
atcgaaggca aggaagctga aactccagtt aaggtcggtt aa                      1002

<210> SEQ ID NO 5
<211> LENGTH: 333
<212> TYPE: PRT
<213> ORGANISM: Artificial Sequence
<220> FEATURE:
<223> OTHER INFORMATION: Synthetic d-ldh mutation 2

<400> SEQUENCE: 5

Met Thr Lys Ile Phe Ala Tyr Ala Ile Arg Glu Asp Glu Lys Pro Phe
1               5                   10                  15

Leu Lys Glu Trp Glu Asp Ala His Lys Asp Val Glu Val Glu Tyr Thr
            20                  25                  30

Asp Lys Leu Leu Thr Pro Glu Thr Ala Ala Leu Ala Lys Gly Ala Asp
        35                  40                  45

Gly Val Val Val Tyr Gln Gln Leu Asp Tyr Thr Ala Glu Thr Leu Gln
    50                  55                  60
```

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                 85                  90                  95

Thr Asn Val Pro Val Tyr Ser Pro Asn Ala Ile Ala Glu His Ala Ala
            100                 105                 110

Ile Gln Ala Ala Arg Ile Leu Arg Gln Ala Lys Ala Met Asp Glu Lys
        115                 120                 125

Val Ala Arg His Asp Leu Arg Trp Ala Pro Thr Ile Gly Arg Glu Val
130                 135                 140

Arg Asp Gln Val Val Gly Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Lys
210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
            260                 265                 270

Trp Glu Gly Lys Glu Phe Pro Asp Ala Arg Leu Ala Asp Leu Ile Ala
        275                 280                 285

Arg Pro Asn Val Leu Val Thr Pro His Thr Ala Phe Tyr Thr Thr His
290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Gln Val Lys Val Gly
                325                 330

<210> SEQ ID NO 6
<211> LENGTH: 1002
<212> TYPE: DNA
<213> ORGANISM: Artificial Sequence
<220> FEATURE:
<223> OTHER INFORMATION: Synthetic d-ldh mutation 2

<400> SEQUENCE: 6
atgactaaaa tcttcgctta cgctataaga gaggacgaaa agccattttt gaaagagtgg      60
gaggatgcgc ataaagatgt tgaagttgag tacacggata acttttaac tcctgaaact     120 gctgcattgg caaagggtgc agacggcgta gtagtatatc aacagcttga ttatacagct     180
gaaaccctcc aagctctcgc tgataatggg attacaaaaa tgtctttgcg taatgtaggt     240
gttgacaaca tagacatggc caaagcaaag gaactaggct tcaaatcac aaatgtgcct     300 gtgtactcac caaatgctat cgctgaacac gctgccatac aagccgctag aatcttaaga     360
caggcgaagg ctatggatga aaaggttgca agacatgatc taagatgggc tcctactatc     420
ggtagggaag taagagatca agttgtcggt gtggtgggaa caggacatat tggccaagtt     480
ttcatgcaga ttatggaagg attcggggca aaagtcattg cctacgacat ttttcgaaac     540

| | | |
|---|---|---|
| cctgagctgg agaaaaaggg ttactacgtt gattctctgg atgacctata caaacaagca | 600 |
| gatgttattt ctcttcatgt gccagatgtc ccagcaaatg tccacatgat caacgacaaa | 660 |
| tcaattgcca agatgaaaca agatgtcgta atcgttaatg tgagtagagg gcctttggtt | 720 |
| gacaccgacg ctgttataag gggtttggat tccggtaaag tatttggata tgcgatggat | 780 |
| gtttacgaag gtgaagtcgg tgtctttaac gaagattggg aaggcaaaga gttcccagac | 840 |
| gcaagattag ccgatttgat cgcaagacca aatgttttag taacaccaca cactgccttc | 900 |
| tatacaacac atgccgtgag aaacatggtt attaaggcat tgataataa cttagaattg | 960 |
| atcgaaggca aggaagctga aactcaagtt aaggtcggtt aa | 1002 |

<210> SEQ ID NO 7
<211> LENGTH: 602
<212> TYPE: PRT
<213> ORGANISM: Escherichia coli

<400> SEQUENCE: 7

```
Met Gln Thr Phe Gln Ala Asp Leu Ala Ile Val Gly Ala Gly Gly Ala
  1               5                  10                  15
Gly Leu Arg Ala Ala Ile Ala Ala Gln Ala Asn Pro Asn Ala Lys
             20                  25                  30
Ile Ala Leu Ile Ser Lys Val Tyr Pro Met Arg Ser His Thr Val Ala
         35                  40                  45
Ala Glu Gly Gly Ser Ala Ala Val Ala Gln Asp His Asp Ser Phe Glu
     50                  55                  60
Tyr His Phe His Asp Thr Val Ala Gly Gly Asp Trp Leu Cys Glu Gln
 65                  70                  75                  80
Asp Val Val Asp Tyr Phe Val His His Cys Pro Thr Glu Met Thr Gln
                 85                  90                  95
Leu Glu Leu Trp Gly Cys Pro Trp Ser Arg Arg Pro Asp Gly Ser Val
            100                 105                 110
Asn Val Arg Arg Phe Gly Gly Met Lys Ile Glu Arg Thr Trp Phe Ala
        115                 120                 125
Ala Asp Lys Thr Gly Phe His Met Leu His Thr Leu Phe Gln Thr Ser
    130                 135                 140
Leu Gln Phe Pro Gln Ile Gln Arg Phe Asp Glu His Phe Val Leu Asp
145                 150                 155                 160
Ile Leu Val Asp Asp Gly His Val Arg Gly Leu Val Ala Met Asn Met
                165                 170                 175
Met Glu Gly Thr Leu Val Gln Ile Arg Ala Asn Ala Val Val Met Ala
            180                 185                 190
Thr Gly Gly Ala Gly Arg Val Tyr Arg Tyr Asn Thr Asn Gly Gly Ile
        195                 200                 205
Val Thr Gly Asp Gly Met Gly Met Ala Leu Ser His Gly Val Pro Leu
    210                 215                 220
Arg Asp Met Glu Phe Val Gln Tyr His Pro Thr Gly Leu Pro Gly Ser
225                 230                 235                 240
Gly Ile Leu Met Thr Glu Gly Cys Arg Gly Glu Gly Gly Ile Leu Val
                245                 250                 255
Asn Lys Asn Gly Tyr Arg Tyr Leu Gln Asp Tyr Gly Met Gly Pro Glu
            260                 265                 270
Thr Pro Leu Gly Glu Pro Lys Asn Lys Tyr Met Glu Leu Gly Pro Arg
        275                 280                 285
```

Asp Lys Val Ser Gln Ala Phe Trp His Glu Trp Arg Lys Gly Asn Thr
290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
                340                 345                 350

Pro Thr Ala His Tyr Thr Met Gly Gly Ile Glu Thr Asp Gln Asn Cys
                355                 360                 365

Glu Thr Arg Ile Lys Gly Leu Phe Ala Val Gly Glu Cys Ser Ser Val
370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
                420                 425                 430

Val Glu Gln Arg Leu Lys Asp Leu Val Asn Gln Asp Gly Gly Glu Asn
                435                 440                 445

Trp Ala Lys Ile Arg Asp Glu Met Gly Leu Ala Met Glu Glu Gly Cys
450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
                500                 505                 510

Leu Asn Val Ala Glu Cys Met Ala His Ser Ala Met Ala Arg Lys Glu
                515                 520                 525

Ser Arg Gly Ala His Gln Arg Leu Asp Glu Gly Cys Thr Glu Arg Asp
530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
                580                 585                 590

Ala Ala Asn Lys Lys Glu Lys Ala Asn Gly
                595                 600

<210> SEQ ID NO 8
<211> LENGTH: 1809
<212> TYPE: DNA
<213> ORGANISM: Escherichia coli

<400> SEQUENCE: 8
gtgcaaacct tcaagccga tcttgccatt gtaggcgccg gtggcgcggg attacgtgct      60
gcaattgctg ccgcgcaggc aaatccgaat gcaaaaatcg cactaatctc aaaagtatac     120
ccgatgcgta gccataccgt tgctgcagaa gggggctccg ccgctgtcgc gcaggatcat     180
gacagcttcg aatatcactt tcacgataca gtagcgggtg cgactggtt gtgtgagcag     240 gatgtcgtgg attatttcgt ccaccactgc ccaaccgaaa tgacccaact ggaactgtgg     300
ggatgcccat ggagccgtcg cccggatggt agcgtcaacg tacgtcgctt cggcggcatg     360
aaaatcgagc gcacctggtt cgccgccgat aagaccggct tccatatgct gcacacgctg    420
ttccagacct ctctgcaatt cccgcagatc cagcgttttg cgaacatttt cgtgctggat    480
attctggttg atgatggtca tgttcgcggc ctggtagcaa tgaacatgat ggaaggcacg    540
ctggtgcaga tccgtgctaa cgcggtcgtt atggctactg gcggtgcggg tcgcgtttat    600
cgttacaaca ccaacggcgg catcgttacc ggtgacggta tgggtatggc gctaagccac    660
ggcgttccgc tgcgtgacat ggaattcgtt cagtatcacc caaccggtct gccaggttcc    720
ggtatcctga tgaccgaagg ttgccgcggt gaaggcggta ttctggtcaa caaaaatggc    780
taccgttatc tgcaagatta cggcatgggc cggaaactc cgctgggcga ccgaaaaac    840
aaatatatgg aactgggtcc acgcgacaaa gtctctcagg ccttctggca cgaatggcgt    900
aaaggcaaca ccatctccac gccgcgtggc gatgtggttt atctcgactt cgtcacctc    960
ggcgagaaaa aactgcatga acgtctgccg ttcatctgcg aactggcgaa agcgtacgtt   1020
ggcgtcgatc cggttaaaga accgattccg gtacgtccga ccgcacacta ccatgggc   1080
ggtatcgaaa ccgatcagaa ctgtgaaacc cgcattaaag gtctgttcgc cgtgggtgaa   1140
tgttcctctg ttggtctgca cggtgcaaac cgtctgggtt ctaactccct ggcggaactg   1200
gtggtcttcg gccgtctggc cggtgaacaa gcgacagagc gtgcagcaac tgccggtaat   1260
ggcaacgaag cggcaattga agcgcaggca gctggcgttg aacaacgtct gaaagatctg   1320
gttaaccagg atggcggcga aaactgggcg aagatccgcg acgaaatggg cctggctatg   1380
gaagaaggct gcggtatcta ccgtacgccg gaactgatgc agaaaaccat cgacaagctg   1440
gcagagctgc aggaacgctt caagcgcgtg cgcatcaccg acacttccag cgtgttcaac   1500
accgacctgc tctacaccat tgaactgggc cacggtctga cgttgctga atgtatggcg   1560
cactccgcaa tggcacgtaa agagtcccgc ggcgcgcacc agcgtctgga cgaaggttgc   1620
accgagcgtg acgacgtcaa cttcctcaaa cacaccctcg ccttccgcga tgctgatggc   1680
acgactcgcc tggagtacag cgacgtgaag attactacgc tgccgccagc taaacgcgtt   1740
tacggtggcg aagcggatgc agccgataag gcggaagcag ccaataagaa ggagaaggcg   1800
aatggctga                                                           1809

<210> SEQ ID NO 9
<211> LENGTH: 891
<212> TYPE: PRT
<213> ORGANISM: Escherichia coli

<400> SEQUENCE: 9

Met Ala Val Thr Asn Val Ala Glu Leu Asn Ala Leu Val Glu Arg Val
 1               5                  10                  15

Lys Lys Ala Gln Arg Glu Tyr Ala Ser Phe Thr Gln Glu Gln Val Asp
             20                  25                  30

Lys Ile Phe Arg Ala Ala Ala Leu Ala Ala Ala Asp Ala Arg Ile Pro
         35                  40                  45

Leu Ala Lys Met Ala Val Ala Glu Ser Gly Met Gly Ile Val Glu Asp
     50                  55                  60

Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Asp Thr Phe Gly
                 85                  90                  95

Thr Ile Thr Ile Ala Glu Pro Ile Gly Ile Ile Cys Gly Ile Val Pro
            100                 105                 110

```
Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525
```

-continued

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
                610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
                770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 10
<211> LENGTH: 2676
<212> TYPE: DNA
<213> ORGANISM: Escherichia coli

<400> SEQUENCE: 10
atggctgtta ctaatgtcgc tgaacttaac gcactcgtag agcgtgtaaa aaaagcccag    60

-continued

| | |
|---|---|
| cgtgaatatg ccagtttcac tcaagagcaa gtagacaaaa tcttccgcgc cgccgctctg | 120 |
| gctgctgcag atgctcgaat cccactcgcg aaaatggccg ttgccgaatc cggcatgggt | 180 |
| atcgtcgaag ataaagtgat caaaaaccac tttgcttctg aatatatcta caacgcctat | 240 |
| aaagatgaaa aaacctgtgg tgttctgtct gaagacgaca cttttggtac catcactatc | 300 |
| gctgaaccaa tcggtattat ttgcggtatc gttccgacca ctaacccgac ttcaactgct | 360 |
| atcttcaaat cgctgatcag tctgaagacc cgtaacgcca ttatcttctc cccgcacccg | 420 |
| cgtgcaaaag atgccaccaa caaagcggct gatatcgttc tgcaggctgc tatcgctgcc | 480 |
| ggtgctccga agatctgat cggctggatc gatcaacctt ctgttgaact gtctaacgca | 540 |
| ctgatgcacc acccagacat caacctgatc ctcgcgactg gtggtccggg catggttaaa | 600 |
| gccgcataca gctccggtaa accagctatc ggtgtaggcg cgggcaacac tccagttgtt | 660 |
| atcgatgaaa ctgctgatat caaacgtgca gttgcatctg tactgatgtc caaaaccttc | 720 |
| gacaacggcg taatctgtgc ttctgaacag tctgttgttg ttgttgactc tgtttatgac | 780 |
| gctgtacgtg aacgttttgc aacccacggc ggctatctgt tgcagggtaa agagctgaaa | 840 |
| gctgttcagg atgttatcct gaaaaacggt gcgctgaacg cggctatcgt tggtcagcca | 900 |
| gcctataaaa ttgctgaact ggcaggcttc tctgtaccag aaaacaccaa gattctgatc | 960 |
| ggtgaagtga ccgttgttga tgaaagcgaa ccgttcgcac atgaaaaact gtccccgact | 1020 |
| ctggcaatgt accgcgctaa agatttcgaa gacgcgtag aaaaagcaga gaactggtt | 1080 |
| gctatgggcg gtatcggtca tacctcttgc ctgtacactg accaggataa ccaaccggct | 1140 |
| cgcgtttctt acttcggtca gaaaatgaaa acggctcgta tcctgattaa caccccagcg | 1200 |
| tctcagggtg gtatcggtga cctgtataac ttcaaactcg caccttccct gactctgggt | 1260 |
| tgtgttctt ggggtggtaa ctccatctct gaaaacgttg gtccgaaaca cctgatcaac | 1320 |
| aagaaaaccg ttgctaagcg agctgaaaac atgttgtggc acaaacttcc gaaatctatc | 1380 |
| tacttccgcc gtggctccct gccaatcgcg ctggatgaag tgattactga tggccacaaa | 1440 |
| cgtgcgctca tcgtgactga ccgcttcctg ttcaacaatg gttatgctga tcagatcact | 1500 |
| tccgtactga aagcagcagg cgttgaaact gaagtcttct tcgaagtaga agcggacccg | 1560 |
| accctgagca tcgttcgtaa aggtgcagaa ctggcaaact ccttcaaacc agacgtgatt | 1620 |
| atcgcgctgg gtggtggttc cccgatggac gccgcgaaga tcatgtgggt tatgtacgaa | 1680 |
| catccggaaa ctcacttcga agagctggcg ctgcgctta tggatatccg taaacgtatc | 1740 |
| tacaagttcc cgaaaatggg cgtgaaagcg aaaatgatcg ctgtcaccac cacttctggt | 1800 |
| acaggttctg aagtcactcc gtttgcggtt gtaactgacg acgctactgg tcagaaatat | 1860 |
| ccgctggcag actatgcgct gactccggat atggcgattg tcgacgccaa cctggttatg | 1920 |
| gacatgccga gtccctgtg tgctttcggt ggtctggacg cagtaactca cgccatggaa | 1980 |
| gcttatgttt ctgtactggc atctgagttc tctgatggtc aggctctgca ggcactgaaa | 2040 |
| ctgctgaaag aatatctgcc agcgtcctac acgaagggt ctaaaaatcc ggtagcgcgt | 2100 |
| gaacgtgttc acagtgcagc gactatcgcg ggtatcgcgt ttgcgaacgc cttcctgggt | 2160 |
| gtatgtcact caatggcgca caaactgggt tcccagttcc atattccgca cggtctggca | 2220 |
| aacgccctgc tgatttgtaa cgttattcgc tacaatgcga acgacaaccc gaccaagcag | 2280 |
| actgcattca gccagtatga ccgtccgcag gctgccgtc gttatgctga aattgccgac | 2340 |
| cacttgggtc tgagcgcacc gggcgaccgt actgctgcta agatcgagaa actgctggca | 2400 |
| tggctggaaa cgctgaaagc tgaactgggt attccgaaat ctatccgtga agctggcgtt | 2460 |

```
caggaagcag acttcctggc gaacgtggat aaactgtctg aagatgcgtt cgatgaccag    2520
tgcaccggcg ctaacccgcg ttacccgctg atctccgagc tgaaacagat cctgctggat    2580
acctactacg gtcgtgatta tgtagaaggt gaaactgcag cgaaaaaaga agccgctccg    2640
gctaaagctg agaaaaaagc gaaaaaatcc gcttaa                              2676

<210> SEQ ID NO 11
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 11
ttcgcggcca cctacgccgc tatctttgca acaactatct gcgataactc agcaaatttt      60
gcatattcgt gttgcagtat tgcgataatg ggagtcttac ttccaacata acggcagaaa     120
gaaatgtgag aaaattttgc atcctttgcc tccgttcaag tatataaagt cggcatgctt     180
gataatcttt ctttccatcc tacattgttc taattattct tattctcctt tattctttcc     240
taacatacca agaaattaat cttctgtcat tcgcttaaac actatatcaa ta            292

<210> SEQ ID NO 12
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 12
atttggcgag cgttggttgg tggatcaagc ccacgcgtag gcaatcctcg agcagatccg      60
ccaggcgtgt atatatagcg tggatggcca ggcaacttta gtgctgacac atacaggcat    120
atatatatgt gtgcgacgac acatgatcat atggcatgca tgtgctctgt atgtatataa    180
aactcttgtt ttcttctttt ctctaaatat tctttcctta tacattagga cctttgcagc    240
ataaattact atacttctat agacacgcaa acacaaatac acacactaa               289

<210> SEQ ID NO 13
<211> LENGTH: 401
<212> TYPE: DNA
<213> ORGANISM: Artificial Sequence
<220> FEATURE:
<223> OTHER INFORMATION: Synthetic TEF1 promoter

<400> SEQUENCE: 13
atagcttcaa aatgtttcta ctccttttt actcttccag attttctcgg actccgcgca      60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180 tcttttttctt cgtcgaaaaa ggcaataaaa atttttatca cgtttctttt tcttgaaaat    240
tttttttttg atttttttct ctttcgatga cctcccattg atatttaagt taataaacgg    300
tcttcaattt ctcaagtttc agtttcattt tcttgttcct attacaactt ttttttacttc    360 ttgctcatta gaaagaaagc atagcaatct aatctaagtt t                       401

<210> SEQ ID NO 14
<211> LENGTH: 798
<212> TYPE: DNA
<213> ORGANISM: Artificial Sequence
<220> FEATURE:
```

<223> OTHER INFORMATION: Synthetic PGK1 promoter

<400> SEQUENCE: 14

| | | |
|---|---|---|
| ctttcctctt tttattaacc ttaattttta ttttagattc ctgacttcaa ctcaagacgc | 60 |
| acagatatta taacatctgc ataataggca tttgcaagaa ttactcgtga gtaaggaaag | 120 |
| agtgaggaac tatcgcatac ctgcatttaa agatgccgat ttgggcgcga atcctttatt | 180 |
| ttggcttcac cctcatacta ttatcagggc cagaaaaagg aagtgttttcc ctccttcttg | 240 |
| aattgatgtt accctcataa agcacgtggc ctcttatcga gaaagaaatt accgtcgctc | 300 |
| gtgatttgtt tgcaaaaaga acaaaactga aaaaacccag acacgctcga cttcctgtct | 360 |
| tcctattgat tgcagcttcc aatttcgtca cacaacaagg tcctagcgac ggctcacagg | 420 |
| ttttgtaaca agcaatcgaa ggttctgaa tggcgggaaa gggtttagta ccacatgcta | 480 |
| tgatgcccac tgtgatctcc agagcaaagt tcgttcgatc gtactgttac tctctctctt | 540 |
| tcaaacagaa ttgtccgaat cgtgtgacaa caacagcctg ttctcacaca ctcttttctt | 600 |
| ctaaccaagg gggtggttta gtttagtaga acctcgtgaa acttacattt acatatatat | 660 |
| aaacttgcat aaattggtca atgcaagaaa tacatatttg gtcttttcta attcgtagtt | 720 |
| tttcaagttc ttagatgctt tcttttctc ttttttacag atcatcaagg aagtaattat | 780 |
| ctactttta caacaaat | 798 |

<210> SEQ ID NO 15
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 15

| | | |
|---|---|---|
| agtttatcat tatcaatact cgccatttca aagaatacgt aaataattaa tagtagtgat | 60 |
| tttcctaact ttatttagtc aaaaaattag ccttttaatt ctgctgtaac ccgtacatgc | 120 |
| ccaaaatagg gggcgggtta cacagaatat ataacatcgt aggtgtctgg gtgaacagtt | 180 |
| tattcctggc atccactaaa tataatggag cccgctttt aagctggcat ccagaaaaaa | 240 |
| aaagaatccc agcaccaaaa tattgttttc ttcaccaacc atcagttcat aggtccattc | 300 |
| tcttagcgca actacagaga acaggggcac aaacaggcaa aaaacgggca caacctcaat | 360 |
| ggagtgatgc aacctgcctg gagtaaatga tgacacaagg caattgaccc acgcatgtat | 420 |
| ctatctcatt ttcttacacc ttctattacc ttctgctctc tctgatttgg aaaaagctga | 480 |
| aaaaaaggt tgaaccagt tccctgaaat tattcccta cttgactaat aagtatataa | 540 |
| agacggtagg tattgattgt aattctgtaa atctatttct taaacttctt aaattctact | 600 |
| tttatagtta gtcttttttt tagttttaaa acaccagaac ttagtttcga cggat | 655 |

<210> SEQ ID NO 16
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 16

| | | |
|---|---|---|
| gccgggatcg aagaaatgat ggtaaatgaa ataggaaatc aaggagcatg aaggcaaaag | 60 |
| acaaatataa gggtcgaacg aaaaataaag tgaaagtgt tgatatgatg tatttggctt | 120 |
| tgcggcgccg aaaaaacgag tttacgcaat tgcacaatca tgctgactct gtggcggacc | 180 |

```
cgcgctcttg ccggcccggc gataacgctg ggcgtgaggc tgtgcccggc ggagtttttt      240
gcgcctgcat tttccaaggt ttaccctgcg ctaaggggcg agattggaga agcaataaga      300
atgccggttg gggttgcgat gatgacgacc acgacaactg gtgtcattat ttaagttgcc      360
gaaagaacct gagtgcattt gcaacatgag tatactagaa gaatgagcca agacttgcga      420
gacgcgagtt tgccggtggt gcgaacaata gagcgaccat gaccttgaag gtgagacgcg      480
cataaccgct agagtacttt gaagaggaaa cagcaatagg gttgctacca gtataaatag      540
acaggtacat acaacactgg aaatggttgt ctgtttgagt acgctttcaa ttcatttggg      600
tgtgcacttt attatgttac aatatggaag ggaactttac acttctccta tgcacatata      660
ttaattaaag tccaatgcta gtagagaagg ggggtaacac ccctccgcgc tcttttccga      720
tttttttcta aaccgtggaa tatttcggat atccttttgt tgtttccggg tgtacaatat      780
ggacttcctc ttttctggca accaaaccca tacatcggga ttcctataat accttcgttg      840
gtctccctaa catgtaggtg gcggagggga gatatacaat agaacagata ccagacaaga      900
cataatgggc taaacaagac tacaccaatt acactgcctc attgatggtg gtacataacg      960
aactaatact gtagccctag acttgatagc catcatcata tcgaagtttc actacccttt     1020
ttccatttgc catctattga agtaataata ggcgcatgca acttcttttc ttttttttc      1080 ttttctctct cccccgttgt tgtctcacca tatccgcaat gacaaaaaaa tgatggaaga     1140
cactaaagga aaaaattaac gacaaagaca gcaccaacag atgtcgttgt tccagagctg     1200
atgaggggta tctcgaagca cacgaaactt tttccttcct tcattcacgc acactactct     1260
ctaatgagca acggtatacg gccttccttc cagttacttg aatttgaaat aaaaaaaagt     1320
ttgctgtctt gctatcaagt ataaatagac ctgcaattat taatcttttg tttcctcgtc     1380
attgttctcg ttcccttcct tccttgtttc tttttctgca caatatttca agctatacca     1440
agcatacaat caactccaag ctggccgc                                         1468

<210> SEQ ID NO 17
<211> LENGTH: 252
<212> TYPE: DNA
<213> ORGANISM: Artificial Sequence
<220> FEATURE:
<223> OTHER INFORMATION: Synthetic CYC1 terminator
<220> FEATURE:
<221> NAME/KEY: misc_feature
<222> LOCATION: (1)..(252)
<223> OTHER INFORMATION: deoxynucleotide sequence (DNA)

<400> SEQUENCE: 17
tcatgtaatt agttatgtca cgcttacatt cacgccctcc ccccacatcc gctctaaccg       60
aaaaggaagg agttagacaa cctgaagtct aggtccctat ttatttttt atagttatgt      120 tagtattaag aacgttattt atatttcaaa ttttttcttt ttttctgtac agacgcgtgt      180
acgcatgtaa cattatactg aaaaccttgc ttgagaaggt tttgggacgc tcgaaggctt      240
taatttgcgg cc                                                          252

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
```

```
atgactaaaa tcttcgctta cg                                              22
```

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19

```
aaaacagcca agcttttaac cgaccttaac tggag                                35
```

<210> SEQ ID NO 20
<211> LENGTH: 71
<212> TYPE: DNA
<213> ORGANISM: Artificial Sequence
<220> FEATURE:
<223> OTHER INFORMATION: primer

<400> SEQUENCE: 20

```
atgaaactcg ccgtttatag cacaaaacag tacgacaaga agtacctgca taggtgacac     60
tatagaacgc g                                                          71
```

<210> SEQ ID NO 21
<211> LENGTH: 70
<212> TYPE: DNA
<213> ORGANISM: Artificial Sequence
<220> FEATURE:
<223> OTHER INFORMATION: primer

<400> SEQUENCE: 21

```
ttaaaccagt tcgttcgggc aggtttcgcc tttttccaga ttgcttaagt tagtggatct     60
gatgggtacc                                                            70
```

<210> SEQ ID NO 22
<211> LENGTH: 71
<212> TYPE: DNA
<213> ORGANISM: Artificial Sequence
<220> FEATURE:
<223> OTHER INFORMATION: primer

<400> SEQUENCE: 22

```
atggctgtta ctaatgtcgc tgaacttaac gcactcgtag agcgtgtaaa taggtgacac     60
tatagaacgc g                                                          71
```

<210> SEQ ID NO 23
<211> LENGTH: 70
<212> TYPE: DNA
<213> ORGANISM: Artificial Sequence
<220> FEATURE:
<223> OTHER INFORMATION: primer

<400> SEQUENCE: 23

```
ttaagcggat tttttcgctt ttttctcagc tttagccgga gcggcttctt tagtggatct     60
gatgggtacc                                                            70
```

<210> SEQ ID NO 24
<211> LENGTH: 71
<212> TYPE: DNA
<213> ORGANISM: Artificial Sequence
<220> FEATURE:
<223> OTHER INFORMATION: primer

<400> SEQUENCE: 24

```
gtgcaaacct tcaagccga tcttgccatt gtaggcgccg gtggcgcggg taggtgacac      60
tatagaacgc g                                                         71

<210> SEQ ID NO 25
<211> LENGTH: 70
<212> TYPE: DNA
<213> ORGANISM: Artificial Sequence
<220> FEATURE:
<223> OTHER INFORMATION: primer

<400> SEQUENCE: 25
ttagcgtggt tcagggtcg cgataagaaa gtctttcgaa ctttctactt tagtggatct      60
gatgggtacc                                                           70

<210> SEQ ID NO 26
<211> LENGTH: 3997
<212> TYPE: DNA
<213> ORGANISM: Artificial Sequence
<220> FEATURE:
<223> OTHER INFORMATION: Synthetic pT7R3H vector

<400> SEQUENCE: 26
atgggcagca gccatcatca tcatcatcac agcagcggcc tggtgccgcg cggcagccat      60
aagcttggct gttttggcgg atgagagaag attttcagcc tgatacagat taaatcagaa     120
cgcagaagcg gtctgataaa acagaatttg cctggcggca gtagcgcggt ggtcccacct     180 gacccccatgc cgaactcaga agtgaaacgc cgtagcgccg atggtagtgt ggggtctccc    240
catgcgagag tagggaactg ccaggcatca aataaaacga aaggctcagt cgaaagactg     300
ggcctttcgt tttatctgtt gtttgtcggt gaacgctctc ctgagtagga caaatccgcc     360
gggagcggat ttgaacgttg cgaagcaacg gcccggaggg tggcgggcag gacgcccgcc     420
ataaactgcc aggcatcaaa ttaagcagaa ggccatcctg acggatggcc ttttttgcgtt    480 tctacaaact cttttttgttt atttttctaa atacattcaa atatgtatcc gctcatgaga     540
caataaccct gataaatgct tcaataatat tgaaaaagga agagtatgag tattcaacat     600
ttccgtgtcg cccttattcc cttttttgcg gcattttgcc ttcctgttttt tgctcaccca     660 gaaacgctgg tgaaagtaaa agatgctgaa gatcagttgg gtgcacgagt gggttacatc     720
gaactggatc tcaacagcgg taagatcctt gagagttttc gccccgaaga acgttttcca     780
atgatgagca cttttaaagt tctgctatgt ggcgcggtat tcccgtgt tgacgccggg      840 caagagcaac tcggtcgccg catacactat tctcagaatg acttggttga gtaattcact     900
ggccgtcgtt ttacaacgtc gtgactggga aaaccctggc gttacccaac ttaatcgcct     960
tgcagcacat cccctttcg ccagctggcg taatagcgaa gaggcccgca ccgatcgccc     1020
ttcccaacag ttgcgggggg gggggaaag ccacgttgtg tctcaaaatc tctgatgtta     1080
cattgcacaa gataaaaata tatcatcatg aacaataaaa ctgtctgctt acataaacag     1140
taatacaagg ggtgttatga gccatattca acgggaaacg tcttgctcga ggccgcgatt     1200
aaattccaac atggatgctg atttatatgg gtataaatgg gctcgcgata atgtcgggca     1260
atcaggtgcg acaatctatc gattgtatgg gaagcccgat gcgccagagt tgtttctgaa     1320
acatggcaaa ggtagcgttg ccaatgatgt tacagatgag atggtcagac taaactggct     1380
gacggaattt atgcctcttc cgaccatcaa gcatttatc cgtactcctg atgatgcatg     1440
gttactcacc actgcgatcc ccgggaaaac agcattccag gtattagaag aatatcctga     1500
```

-continued

```
ttcaggtgaa aatattgttg atgcgctggc agtgttcctg cgccggttgc attcgattcc    1560
tgtttgtaat tgtcctttta acagcgatcg cgtatttcgt ctcgctcagg cgcaatcacg    1620
aatgaataac ggtttggttg atgcgagtga ttttgatgac gagcgtaatg gctggcctgt    1680
tgaacaagtc tggaaagaaa tgcataagct tttgccattc tcaccggatt cagtcgtcac    1740
tcatggtgat ttctcacttg ataaccttat ttttgacgag gggaaattaa taggttgtat    1800
tgatgttgga cgagtcggaa tcgcagaccg ataccaggat cttgccatcc tatgaactg     1860 cctcggtgag ttttctcctt cattacagaa acggcttttt caaaaatatg gtattgataa    1920
tcctgatatg aataaattgc agtttcattt gatgctcgat gagttttctt aatcagaatt    1980
ggttaattgg ttgtaacact ggcagagcat tacgctgact tgacgggacg gcggctttgt    2040
tgaataaatc gaacttttgc tgagttgaag gatcagatca cgcatcttcc cgacaacgca    2100
gaccgttccg tggcaaagca aaagttcaaa atcaccaact ggtccaccta caacaaagct    2160
ctcatcaacc gtggctccct cactttctgg ctggatgatg gggcgattca ggcctggtat    2220
gagtcagcaa caccttcttc acgaggcaga cctcagcgcc cccccccccc gcaaactatt    2280
aactggcgaa ctacttactc tagcttcccg gcaacaatta atagactgga tggaggcgga    2340
taaagttgca ggaccacttc tgcgctcggc ccttccggct ggctggttta ttgctgataa    2400
atctggagcc ggtgagcgtg ggtctcgcgg tatcattgca gcactggggc cagatggtaa    2460
gccctcccgt atcgtagtta tctacacgac ggggagtcag gcaactatgg atgaacgaaa    2520
tagacagatc gctgagatag gtgcctcact gattaagcat tggtaactgt cagaccaagt    2580
ttactcatat atactttaga ttgatttaaa acttcatttt taatttaaaa ggatctaggt    2640
gaagatcctt tttgataatc tcatgaccaa atcccttaa cgtgagtttt cgttccactg     2700
agcgtcagac cccttaataa gatgatcttc ttgagatcgt tttggtctgc gcgtaatctc    2760
ttgctctgaa aacgaaaaaa ccgccttgca gggcggtttt tcgaaggttc tctgagctac    2820
caactctttg aaccgaggta actggcttgg aggagcgcag tcaccaaaac ttgtcctttc    2880
agtttagcct taaccggcgc atgacttcaa gactaactcc tctaaatcaa ttaccagtgg    2940
ctgctgccag tggtgctttt gcatgtcttt ccgggttgga ctcaagacga tagttaccgg    3000
ataaggcgca gcggtcggac tgaacggggg gttcgtgcat acagtccagc ttggagcgaa    3060
ctgcctaccc ggaactgagt gtcaggcgtg gaatgagaca aacgcggcca taacagcgga    3120
atgacaccgg taaccgaaa ggcaggaaca ggagagcgca cgagggagcc gccaggggga    3180
aacgcctggt atctttatag tcctgtcggg tttcgccacc actgatttga gcgtcagatt    3240
tcgtgatgct tgtcaggggg gcggagccta tggaaaaacg gctttgccgc ggccctctca    3300
cttccctgtt aagtatcttc ctggcatctt ccaggaaatc tccgcccgt tcgtaagcca     3360 tttccgctcg ccgcagtcga acgaccgagc gtagcgagtc agtgagcgag gaagcggaat    3420
atatcctgta tcacatattc tgctgacgca ccggtgcagc cttttttctc ctgccacatg    3480
aagcacttca ctgacaccct catcagtgcc aacatagtaa gccagtatac actccgctag    3540
caaggagatg gcgcccaaca gtcccccggc cacgggcct gccaccatac ccacgccgaa     3600
acaagcgctc atgagcccga agtggcgagc ccgatcttcc ccatcggtga tgtcggcgat    3660
ataggcgcca gcaaccgcac ctgtggcgcc ggtgatgccg gccacgatgc gtccggcgta    3720
gaggatccgg agcttatcga cctgattctg tggataaccg tattaccgcc tttgagtgag    3780
ctgataccgc tcgccgcagc cgaacgaccg agcgcagcga gtcagtgagc gaggaagcgg    3840
aagagcgccc aatacgcaaa ccgcctctcc ccgcgcgttg gccgattcat taatgcagga    3900
```

```
tctcgatccc gcgaaattaa tacgactcac tatagggaga ccacaacggt ttccctctag    3960
aaataatttt gtttaacttt aagaaggcga tatacat                              3997
```